United States Patent [19]

Ellison

[11] Plant 5,187

[45] Jan. 31, 1984

[54] ASPARAGUS PLANT

[75] Inventor: J. Howard Ellison, Milltown, N.J.

[73] Assignee: Research Corporation, New York, N.Y.

[21] Appl. No.: 226,922

[22] Filed: Jan. 21, 1981

[51] Int. Cl.[3] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

An asparagus plant having female characteristics, originating from the Mary Washington cultivar, which has been found suitable for use in production of edible spears and of hybrid seed because of its ability to transmit rust resistance, high yield and good field tolerance to root rot as well as crown rot which would otherwise limit production, enabling growth where standard susceptible cultivars are not profitably grown.

2 Drawing Figures

BACKGROUND OF THE INVENTION

This invention relates to a new and distinct variety of asparagus plant, and specifically to one which I denominate as No. 51 in my records, being a female variety and of particular value as will be set forth hereinafter in relation to the production of edible spears and hybrid seed, specifically a hybrid variety which has outstanding characteristics attributable to this particular plant and to another variety which I have developed.

The program of asparagus improvement which I have carried out over a period of many years is the result of the decline in asparagus production caused by a number of different problems, such as root rot (*Fusarium oxysporum*), and crown rot (*F. moniliforme*). At the same time I have endeavored to select and provide a plant which will be more productive than those heretofore known, in this instance the variety hereof having originated from a Mary Washington cultivar (unpatented).

As those familiar with the art well know, the aspect of increasing disease resistance in asparagus to counter wide spread infection with the fungus Fusarium significantly affects yield. Over the years such infection has reduced production to a point where drastic improvement is necessary to make the growing of asparagus profitable.

In my intensive program of breeding and selection, which has taken place in the vicinity of New Brunswick, N.J., I have devoted my skill and knowledge to development and selection of male and female plants which are resistant to the various problems associated with asparagus growth on a production basis, in an endeavor to provide an ultimate asparagus plant which is highly productive, and resistant to root rot and crown rot problems which currently exist.

The Mary Washington cultivar, long grown and initially a very productive and valuable plant has been permitted to determine in all areas by reason of the gathering of seeds indiscriminately from the fields and replanting them, with the ultimate genetic characteristics have deteriorated to a point which reduced production and thus required that something be done to restore production of commercial asparagus.

As indicated, the particular female plant hereof was found in a very old cultivated field of Mary Washington plants, near Greenwich, N.J., being one of those in a group selected at that time, and subsequently in turn observed and by careful reproduction resulted in the ultimate variety hereof, which exhibits high yield of edible spears and transmits high yielding ability to hybrids along with good field tolerance to rust, root rot and crown rot.

Genetic transmittance of high yield and tolerance to these disease problems would certainly be valuable to farmers who desire to grow a hybrid where standard susceptible cultivars will not grow profitably.

It is notable that the instant plant has a number of distinctive characteristics best summarized in a numerical table which is included herewith and which will be referred to subsequently. While asparagus plants in general are of similar color in most aspects, there are some distinguishing characteristics which make them susceptible of identification thereby.

In the selection of this particular variety which I have denominated No. 51, it is notable that the stalks are quite round in cross-section, as compared with other varieties. The variety does in fact transmit those desirable characteristics previously mentioned.

Referring to the data which I have caused to be accumulated over a period of time, and which is representative of the particular variety under consideration and which I have selected for that reason, the same is set forth as follows:

Number of nodes below first branch—22.3;
Number of cm from crown to first branch—70.4;
Number of branches—60.2;
Number of cm between first and last branch—163.8;
Number of cladophyll nodes beyond last branch—24.3;
Number of cm beyond last branch—20.2;
Diameter (mm) highest head stalk—24.0;
Diameter (mm) largest stalk—26.8;
Internode length (cm) between branches—2.72;
Internode length (cm) beyond last branch—0.84.

As will be seen from the foregoing, there are in fact measurable characteristics which will serve and have served to enable me to identify the variety hereof, and to ascertain that the same are present in successive asexual propagations which I have performed, specifically by the meristem process and thus consistent with my usual efforts in selecting and breeding asparagus plants of this nature.

Since it is desirable to provide some indication of the configuration and color of the plant, the drawing appended hereto, discloses a typical plant of my new variety as the same is shown by color photography with as near like representation of the plant as is possible to obtain in a color reproduction of this kind. Particularly note that the stalk, being the most critical and notable aspect of the plant, is described as to color with the bloom removed, compared with the Munsell Color Cascade published by MacBeth Division of Kollmorgen Corporation, notation 22-11.8, yellowish green.

The flowers of the plant may be described as including yellow petal tips notation 24-6, with the green rib of the petal 22-10. The yellow petal tip refers to the blossom ends of the petals, approximately half way to the base. The green rib of the petal refers to the mid rib of the petal which extends from the base to approximately three-fourths the length of the petals. The extreme basal portion of the petals also is the same shade of green.

Other colors not described may be observed but this is the primary distinctive color feature of this variety and serves to distinguish the same from other varieties and more particularly from the Mary Washington variety.

The various dimensional notations in the table previously set forth, are considered in the light of the drawing comprising a part hereof which discloses a typical asparagus plant in which the titles of the notations are disclosed.

I have found that identification of asparagus plants which I have developed, may be materially assisted by using this table and in fact affords a basis for distinguishing my new variety from other similar, even related varieties.

I claim:

1. A new and distinct variety of asparagus plant, substantially as herein shown and described, characterized particularly as to novelty by the unique combination of characteristics, rust resistance (to *Puccina asparagi*), good field tolerance to root rot (*Fusarium oxysporum*) and crown rot (*F. moniliforme*) together with its ability to produce edible spears and to be combined with a male plant to produce a hybrid having improved yield in addition to the foregoing.

* * * * *

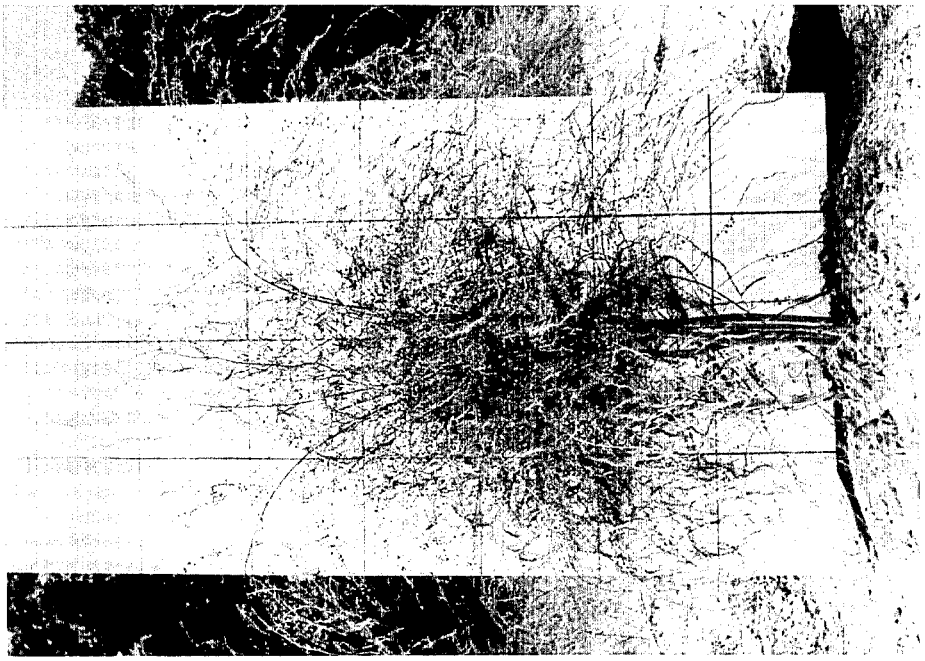
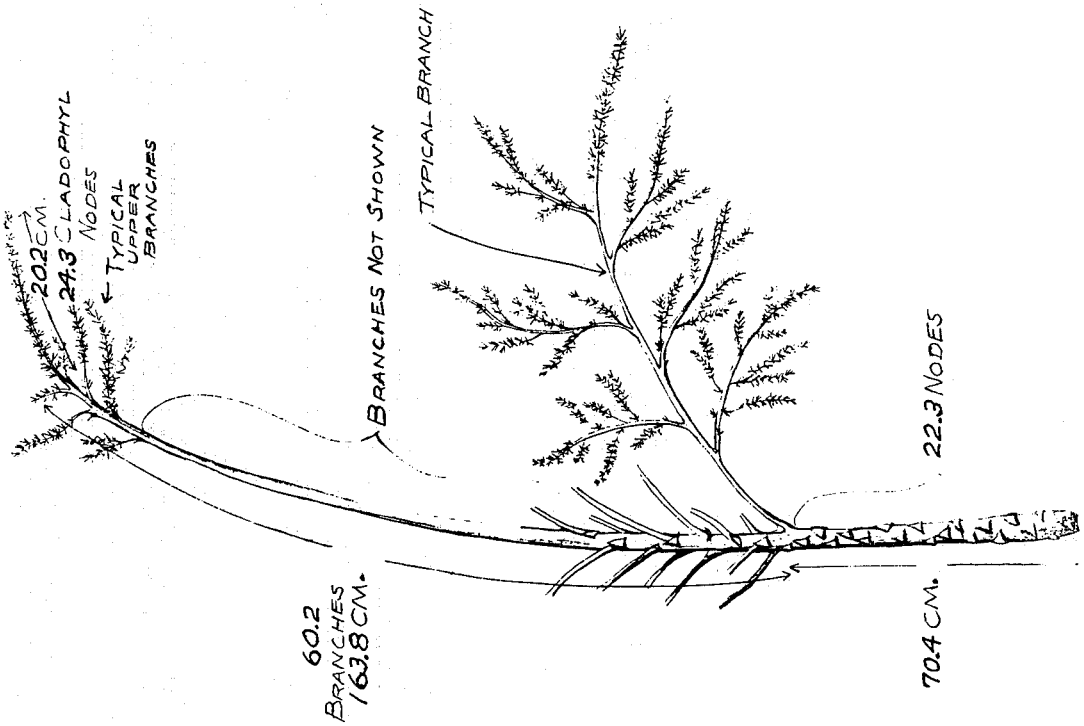
24.3 CLADOPHYL NODES
20.2 CM.
TYPICAL UPPER BRANCHES
BRANCHES NOT SHOWN
TYPICAL BRANCH
60.2 BRANCHES 163.8 CM.
22.3 NODES
70.4 CM.